United States Patent [19]

Langer et al.

[11] Patent Number: 4,888,176

[45] Date of Patent: * Dec. 19, 1989

[54] CONTROLLED DRUG DELIVERY HIGH MOLECULAR WEIGHT POLYANHYDRIDES

[75] Inventors: Robert S. Langer, Sommerville; Abraham J. Domb, Brookline; Cato T. Laurencin, Cambridge, all of Mass.

[73] Assignee: Massachusetts Institute of Technology, Cambridge, Mass.

[*] Notice: The portion of the term of this patent subsequent to Jul. 12, 2005 has been disclaimed.

[21] Appl. No.: 61,294

[22] Filed: Jun. 12, 1987

Related U.S. Application Data

[63] Continuation-in-part of Ser. No. 613,001, May 21, 1984, and a continuation-in-part of Ser. No. 49,988, May 15, 1987, abandoned, which is a continuation-in-part of Ser. No. 892,809, Aug. 1, 1986, said Ser. No. 613,001, is a continuation of Ser. No. 477,710, Mar. 22, 1983, abandoned.

[51] Int. Cl.$^4$ ............................................. A61K 31/74
[52] U.S. Cl. .................................... 424/426; 424/78; 528/176
[58] Field of Search .................... 528/176; 424/426, 78

[56] References Cited

U.S. PATENT DOCUMENTS 3,960,150 6/1976 Hussain ............................... 128/260

OTHER PUBLICATIONS

Yoda et al, vol. 32, No. 10 p. 1120–Bull. Chem. Soc. Japan (1959).
Encylcopedia of Pol. Sci. and Tech, vol. 10 (1969) pp. 630–653.
K. Leong et al, Journal of Biomed Mat. Res. vol. 20, 51–64 (1986).
Linhardt et al, Pol. Preprints 24/ 47–8 1983.

Primary Examiner—Joseph L. Schofer
Assistant Examiner—Peter F. Kulkosky
Attorney, Agent, or Firm—Kilpatrick & Cody

[57] ABSTRACT

A bioerodible controlled drug release device is produced as a homogeneous polymeric matrix from a high molecular weight polyanhydride and a suitable biologically active substance. The high molecular weight polyanhydride is defined by a molecular weight greater than 20,000 and an intrinsic viscosity greater than 0.3 dl/g. The controlled drug release device is preferably formed by solvent casting with the biologically active substance and exhibits zero order release, improved correlation between the rate of release and polymer degradation, and an induction period between introduction to the eroding environment and the initial release of the biologically active substance. The controlled drug release devices are stable for extended periods of time, flexible and durable and not subject to fracture and disintegration.

18 Claims, 19 Drawing Sheets

CONTROLLED DRUG DELIVERY HIGH MOLECULAR WEIGHT POLYANHYDRIDES

CROSS-REFERENCE OF RELATED APPLICATIONS

This application pertains to new and useful improvements to controlled drug delivery high molecular weight polyanhydrides and is a continuation-in-part application of Ser. No. 06/613,001 filed May 24, 1984 which is a continuation of Ser. No. 477,710 filed Mar. 22, 1983, now abandoned, and a continuation-in-part of Ser. No. 049,988 filed May 15, 1987, now abandoned, which is a continuation-in-part of Ser. No. 892,809 filed Aug. 1, 1986.

BACKGROUND OF THE INVENTION

1. Field of the Invention

The present invention relates to the synthesis and preparation of high molecular weight polyanhydrides suitable for use as bioerodible sustained drug release devices. More particularly, the present invention pertains to a sustained drug release implant formed from a thin film of a homogeneous matrix of the novel high molecular weight polyanhydrides and a suitable drug. The novel high molecular weight polyanhydride implants exhibit superior biocompatibility, release and degradation rates without experiencing any polymer to drug interaction. The novel polyanhydrides further exhibit increased chemical stability and have demonstrated superior film forming qualities enabling the polyanhydrides to be used with solvent casting techniques.

2. Description of the Prior Art

In recent years much research has been carried out to develop systems for the controlled release of active agents, especially drugs, over a period of time. In conventional drug delivery, proceeding through various routes of administration, one characteristically sees drug concentration in plasma rise, reach a maximum and fall. The problems encountered with these conventional drug delivery systems include the danger of reaching toxic levels where serious side effects can occur, and conversely the danger of drug concentrations falling to the subtherapeutic level. Efforts to address these problems date to as early as the 1930's, when the concept of sustained drug delivery was introduced in an effort to control the rate of release and maintain a continuous level of drug within the patient.

The purpose of these controlled release systems is to prolong the release of the drug at a controlled constant rate. By controlling the rate of release of the drug the therapeutic effects of the drug are thereby maximized by presenting the drug in a continuous, most beneficial and reliable manner with a minimum possibility of complications due to the fluctuating drug concentration.

The controlled release of drugs can be accomplished by several mechanisms including the complexation with substances such as salts or resins, formation of emulsions or suspensions, compression into dense matrices, and encapsulation using coatings whose dissolution is pH dependent. While such systems have been effective in prolonging drug release, they in general suffer from patient to patient variations and an inability to provide release for periods of time greater than one day. Bioerodible implants offer controlled release of drugs avoiding the disadvantages of the prior art drug release systems while offering the additional advantage of eliminating the need for surgical removal of the device.

The bioerodible drug release systems which have proven most effective are the devices where the drug is uniformly distributed throughout the polymer in a homogeneous matrix. In addition, effective bioerodible systems require that the surface erosion is the only determining factor permitting the drug release to occur. With a constant erosion rate the rate of release of the drug is proportional to the surface area of the system. Preferably the polymeric matrix erodes at a constant preselected rate, with only minimal diffusion, such that the drug is released independently of the concentration of any other chemical component or stimulus. It is therefore necessary to utilize a geometry of the polymeric matrix that does not substantially change its surface area as a function of time in order to obtain zero order release of the drug.

To be useful as a matrix for controlled drug release the polymeric composition must also not undergo bulk erosion which often occurs in addition to or in place of surface erosion. This bulk erosion causes the composition to take on a sponge-like consistency which causes the break-up of the polymeric matrix. Bulk erosion has been shown to directly result from the hydrophilic nature of most bioerodible polymeric compositions. Examples of polymeric matrices which have been shown to undergo bulk erosion include polylactic acid, polyglutamic acid, polycaprolactone and lactic-/glycolic acid copolymers.

One example of the prior art bioerodible drug release polymers employs a polyorthoester composition as described in U.S. Pat. No. 4,070,347. An advantage of the use of polyorthoesters is that hydrolysis of the polymer is pH sensitive and the pH may therefore be used for regulation of the release of the drug. In practice however, the polyorthoesters which have been synthesized have numerous disadvantages which have hindered their use. For example polyorthoesters are often times too hydrolytically stable for use in controlled release systems without acid catalysts being included within the polymeric matrix to promote bioerosion. As a consequence, the polyorthoester polymers tend to swell substantially when attempts are made to suppress degradation in the interior of the matrix. The rate of swelling of the polymer often dominates and affects the rate of release of the drug more than the rate of erosion itself. Additionally, the degradation products are not as simple as some other bioerodible polymers such as polylactic acid which has the advantage of degrading into water and carbon dioxide.

A further example of the prior art controlled drug release devices is described in a recent study by Leong, et al reported in *J. Biomed. Mat. Res.*. Vol. 19, 941–955 (1985). These controlled release devices incorporated a low molecular weight polyanhydride copolymer prepared from mixed prepolymers. Controlled studies have shown that the prior art polyanhydrides produced by known solution polymerization and melt polymerizations to have a weight average molecular weight of a few thousand up to at most 20,000. These prior art polyanhydrides have been limited in their utility as bioerodible implants due to their low molecular weight (generally 12,500) and correspondingly low intrinsic viscosity in solution (approximately 0.1 to 0.3 dl/g in organic solvents at room temperature). Although the prior art polyanhydrides are useful in controlled release drug delivery systems due to their hydrolytic instability and the fact that they degrade into monomeric diacids which are biocompatible as shown by tissue response and toxicological studies, the rate of degradation is too rapid for many applications. In addition, these prior art low molecular weight polyanhydrides have been found to degrade at a rate greater than the rate of release of the drug and begin to disintegrate after approximately 60 percent degradation.

Further disadvantages of the prior art low molecular weight polyanhydrides is the low tensil strength and poor film forming qualities such that the use of low molecular weight polyanhydrides results in a polymeric matrix which is opaque, brittle and incapable of being formed into thin disks or films. Because of the physical limitations of the low molecular weight polyanhydrides the controlled release devices can only be manufactured by pressing the powdered polyanhydride with the drug into a tablet or by melting the polyanhydride with the drug at a relatively high temperature. The first method frequently results in a nonhomogeneous mixture which demonstrates poor release kinetics. Melting the two components tends to cause degradation of the drug and interactions between the drugs and the polyanhydrides.

The generally preferred method of manufacturing biomedical devices is by solvent casting the polymeric material to form films. These films have the advantage of generally providing a more homogeneous distribution of the drug and the ability to be cast as a sheet at ambient temperature thereby providing more desirable release kinetics for the controlled release of the drug. The prior art low molecular weight polyanhydrides, due to their brittle characteristics, low tensil strength, and low viscosity have proven unsatisfactory for such solvent casting techniques.

Other examples of the prior art polyanhydrides are reported *J. Am. Chem. Soc.*, Vol. 52, 4110 (1930) and *J. Am. Chem. Soc.*, Vol. 54, 1569 (1932). Examples of such prior art polymers include poly [bis(p-carboxyphenoxy)alkane anhydrides] which exhibit improved hydrolytic resistance as well as film and fiber forming properties as reported in *Makromol. Chem.*, Vol. 24, 76 (1957). These prior art polyanhydrides have the disadvantage in that they tend to be insoluble in organic solvents, have a low tensil strength and viscosity and thus cannot be solvent cast. Although over 100 different polyanhydrides have been prepared to date, these polyanhydrides have never been commercialized primarily due to the problem of hydrolytic instability.

Some of the prior art polyanhydrides are reported to have molecular weights as high as 20,000 while other prior art polyanhydrides have been reported to have an intrinsic viscosity greater than 0.3 dl/g. The polyanhydrides when prepared according to these disclosed methods seldom produce a high molecular weight having a weight average molecular weight greater than 20,000 or an intrinsic viscosity greater than 0.3 dl/g. The prior art polyanhydrides reported to have the higher molecular weights had a low intrinsic viscosity while those which exhibited the higher intrinsic viscosities had the lower molecular weights. None of the prior art polyanhydrides when prepared according to the disclosed method have been shown to simultaneously have both a weight average molecular weight greater than 20,000 and an intrinsic viscosity greater than 0.3 dl/g. As setforth hereafter in greater detail the combination of both of these characteristics affect the film forming characteristics of the polyanhydrides and it is believed the poor film forming qualities of the prior art polyanhydrides is due to the lower molecular weight and intrinsic viscosity.

There is thus a need for a hydrophobic bioerodible polymeric system capable of providing controlled drug release wherein the erosion products are nontoxic and are readily eliminated or metabolized by the body. In addition, it would be desirable to provide a polymeric system which exhibits good mechanical and physical integrity, includes good film forming characteristics to be adaptable for solvent casting and has a high tensil strength. A suitable polymeric matrix for controlled drug release must further be dense enough to prevent diffusion of the drug, be easy to synthesize and be stable for extended periods of time.

The present invention is directed primarily to a controlled release polymeric matrix utilizing a high molecular weight polyanhydride homogeneously mixed with a suitable drug. The high molecular weight polyanhydride used with the controlled release device is capable of being solvent cast into a variety of shapes and sizes. The novel high molecular weight polyanhydrides of the present invention exhibit transparent, flexible and thin film forming capabilities. In addition, the novel high molecular weight polyanhydride matrices are found to possess a higher density increase in the hydrophobicity of the resulting polymer matrix a more constant rate of degradation and drug release and improved biocompatibility than the prior art low molecular weight polyanhydrides.

SUMMARY OF THE INVENTION

The disadvantages and limitations of the prior art methods and devices for controlled drug delivery are obviated while providing for the controlled delivery of drugs while exhibiting zero order release. The high molecular weight polyanhydrides of the present invention exhibit superior film forming qualities, are flexible and stable for extended periods of time. The use of the novel high molecular weight polyanhydrides for controlled drug release devices further have the advantage of being suitable for solvent casting and do not exhibit any interaction between the polymer and the drug normally encountered at higher temperatures. Bioerodible controlled drug release devices prepared with the novel polymers further have a drug release rate proportional to the degradation of the polymer matrix.

An essential feature in preparing the high molecular weight polyanhydrides is in the use of individually prepared pure prepolymers. It has been demonstrated that impurities normally present in the prior art methods have hindered the extent of polymerization and the molecular weight. These impurities have further been discovered to reduce the biocompatibility of the device upon degradation. Additional essential steps in obtaining the desirable high molecular weights include the careful control of the temperature and reaction time of polymerization under a high vacuum whose dependence on molecular weight have not heretofore been examined and optimized.

The high molecular weight polyanhydrides prepared from the purified isolated prepolymers are especially useful for biomedical applications due to the desired constant bioerodible characteristics of the polymer, the erosion by-products and the superior film forming characteristics.

In the preferred embodiment of the invention, the high molecular weight polyanhydrides are incorporated into a controlled drug release device using solvent casting techniques. To prepare the controlled release device a predetermined quantity of a drug is added to a solution of the copolymer dissolved in a suitable solvent, for example methylene chloride. The solution of drug and copolymer is poured into a glass bowl and frozen after which it is dried under vacuum to remove all traces of solvent. This casting technique produces translucent polyanhydride copolymer films which are suitable for in vivo and in vitro devices which exhibit zero order release, superior biocompatibility and proportional rates of drug release and polymer erosion.

DETAILED DESCRIPTION OF THE INVENTION

Figure 1A:
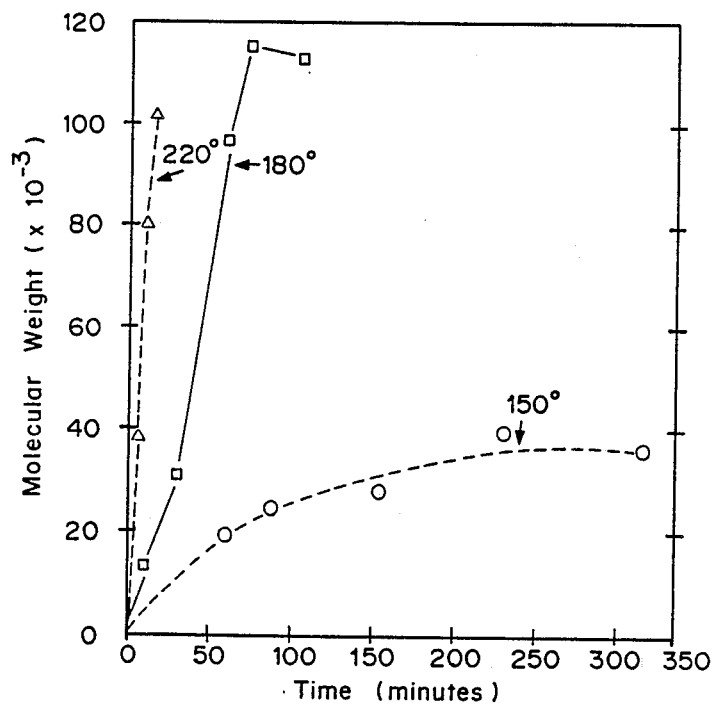
FIG. 1A is a graph of the molecular weight ($\times 10^{-3}$) of CPP:SA (20:80) as a function of temperature (150 degrees C., 180 degrees C., 220 degrees C.) over time in minutes.

The present invention is directed to novel bioerodible controlled drug release devices which are primarily intended to be subcutaneously implanted in the body. The controlled drug release devices of the invention have been found particularly useful for in vitro and in vivo controlled drug release where the implant degrades into components which are easily metabolized by the body. The novel controlled drug release devices exhibit superior biocompatibility compared to the prior art devices and exhibit zero order release of the drug. More particularly, the invention is directed to controlled drug release implants prepared from a homogeneous matrix of novel high molecular weight polyanhydrides having weight average molecular weight greater than 20,000 and an intrinsic viscosity greater than 0.3 dl/g and a suitable drug or other biologically active substance.

The high molecular weight polyanhydrides of the invention, unlike the prior art low molecular weight polyanhydrides, exhibit superior film forming qualities and are therefore easily formed into durable, transparent and flexible devices which are shelf stable for extended periods of time. Additionally, by employing the high molecular weight polyanhydrides the homogeneous matrix can be formed by solvent casting techniques at room temperatures which thereby avoid the degradation of the polymer or the drug due to compression molding or the high temperatures of melt casting techniques previously used. By enabling the use of solvent casting techniques the drug to polymer interaction is also avoided which often occurs in compression molding and melt casting techniques since it is not necessary to heat the polymer or the drug prior to casting.

The high molecular weight polyanhydrides employed in the preparation of the novel bioerodible devices are prepared according to the method outlined in the doctorate thesis titled "Novel Bioerodible Polymers For Controlled Release Analysis Of In Vitro/In Vivo Performance And Characterizations Of Mechanism" by Cato T. Laurencin, 1987 at the Massachusetts Institute of Technology to be published subsequent to this application.

Essentially, the high molecular weight polyanhydride copolymers suitable for use as bioerodible drug release implants are synthesized by melt condensation from a mixture of individually synthesized and purified mixed anhydride prepolymers prepared by heating diacids with acidic anhydride. In order to achieve the high molecular weights it is absolutely necessary to carry out the polymerization steps under controlled optimum conditions. The factors which must be optimized to achieve the high molecular weights include the reaction temperature, purity of the monomers and prepolymers, careful removal of the condensation products under high vacuum and the reaction time to avoid degradation of the polymer. The method according to the present invention is used in the following nonlimiting examples to synthesize anhydride prepolymers which can then be combined and polymerized to form the high molecular weight anhydride copolymers. In the preferred form, individually prepared pure isolated prepolymers are made and purified within two work days. The copolymers are prepared by mixing together and polymerizing under optimum conditions precalculated amounts of the prepolymers.

The high molecular weight copolymer according to the present invention may be synthesized from highly pure isolated prepolymers formed from aliphatic dicarboxylic acids, aromatic-aliphatic dicarboxylic acids, combinations of aromatic, aliphatic and aromatic-aliphatic dicarboxylic acids, aromatic and aliphatic heterocyclic dicarboxylic acids aromatic and aliphatic heterocyclic dicarboxylic acids in combination with aliphatic dicarboxylic acids, aromatic-aliphatic dicarboxylic acids and aromatic dicarboxylic acids of more than one phenyl group.

The preferred high molecular weight carboxylic acids intended for use in biomedical applications are prepared from monomers including bis(p-carboxyphenoxy)alkanes, hydroquinonediacetic acid, 1,4-biscarboxymethylbenzene, 2,2-bis(4-hydroxyphenyl) propane diacetic acid, 2,2-bis(4-carboxyphenyl)propane, terephthalic acid, bis(4-carboxyphenyl alkanes, 1, 4 phenylene dipropionic acid and cyclohexane dicarboxylic acids.

The general method of preparing the high molecular weight polyanhydrides include the steps of refluxing a pure dicarboxylic acid monomer in acetic anhydride for 20 to 90 minutes with the resulting prepolymer purified by recrystalization to remove all traces of acetic anhydride. Precalculated amounts of the purified prepolymers are subjected to a melt polycondensation step under a high vacuum ($10^2$ mm Hg) to remove the acetic anhydride condensation product. The high molecular weight polyanhydride is then further purified prior to formation of the controlled drug release device.

Figure 1B:
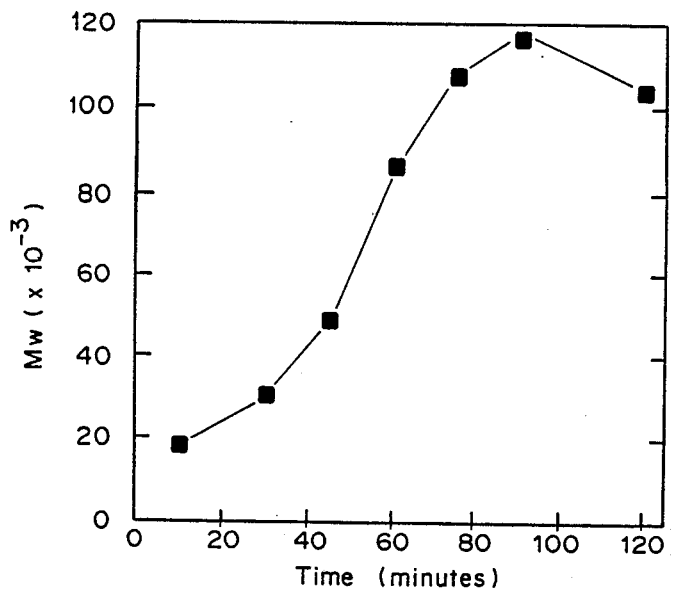
FIG. 1B is a graph of the molecular weight as a function of time during polymerization of CPP:SA (20:80).

In polymerizing the high molecular weight polymers it is essential to carefully follow the controlled parameters of reaction time, temperature and vacuum. As can be seen in the graph of FIG. 1A the maximum molecular weight was achieved at 180 degrees C. and at a reaction time of about 90 minutes. At higher or lower temperatures the molecular weight was not as high as when polymerized at 180° degrees C. Similarly, the reaction time must be limited to prevent decomposition as demonstrated in FIG. 1B which reveals that the molecular weight starts to decrease when the reaction time is carried too far. Test results have further demonstrated that a high vacuum of at least $10^{-2}$ mm Hg is critical to obtain the high molecular weight polyanhydrides.

The following examples are intended to be exemplary only of suitable high molecular weight polyanhydrides and their methods of synthesis.

EXAMPLE I 300 grams of p-hydroxybenzoic acid was dissolved in 900 ml of a warm 2 to 1 mixture of water and acetone and allowed to crystallize at room temperature overnight. In a one liter three neck flask equipped with a mechanical stirrer, a condenser, and a dropping funnel was placed a solution of 138 grams of p-hydroxybenzoic acid and 80 grams of sodium hydroxide in 400 ml of water. Through the funnel, 102 grams of 1,3-dibromopropane was added over a period of 1.5 hours, while the contents of the flask were stirred and kept at reflux temperature. The mixture was refluxed for 3.5 hours followed by the addition of 20 grams of sodium hydroxide which was then refluxed again for 2 hrs. The fine powdery, white precipitate of the disodium salt was isolated by filtration and washed with 200 ml of methanol. The precipitate was dissolved in 1 liter of distilled water and extracted with 200 ml of ether to remove traces of the dibromide using a paper filter. The solution was then acidified using 6N sulphuric acid to a pH less than 2. The diacid was isolated by filtration and after freezing for 2 hrs was dried for 3 days using a lyophilizer yielding 120 grams.

The diacid, carboxyphenoxypropane (CPP) was purified by placing 50 grams in 200 ml of analytical acetone and allowing it to swirl in solution overnight to remove unreacted p-hydroxybenzoic acid.

To prepare the CPP polymer 40 grams of CPP powder was added to 500 ml boiled acidic anhydride at approximately 130 degrees C. under dry nitrogen reflux. The reaction was stopped after 15 min. and the solution was filtered through a filter paper to another 1 liter round bottom flask. The solution was then concentrated to 150 ml by evaporation. The solution was allowed to crystallize which was then separated by filtration and transferred to 200 ml of anhydrous diethyl ether in an erlenmeyer flask and allowed to swirl for several hours at room temperature. The white crystals were separated by filtration and dried in a calcium chloride desicator under vacuum. It is essential that the degree of polymerization of the prepolymer not be greater than 4 by G.C.P.

A sebacic acid prepolymer was prepared by refluxing 60 grams of sebacic acid with 250 ml of acidic anhydride under nitrogen for 90 minutes. The excess acetic anhydride was evaporated from the prepolymer which was then recrystallized from toluene. The crystals were then filtered and recrystallized in a mixture of petroleum ether and anhydrous diethyl ether. The white crystals were then separated by filtration and dried under vacuum.

The high molecular weight polyanhydride copolymer was prepared by mixing 0.8 grams of the CPP prepolymer with the sebacic acid prepolymer in a glass tube with a side arm equipped with a capillary nitrogen inlet. After the prepolymers were melted by imersing the tube in an oil bath at 180 degrees C., a high vacuum (less than $10^{-2}$ mm Hg) was applied through the side arm. The acetic anhydride condensation product was collected in an acetone/dry ice trap. During the polymerization a strong nitrogen sweep with vigorous agitation of the melt was performed for 30 seconds every 15 minutes. After 90 minutes the tube was removed from the oil bath and the viscous polymer was allowed to cool to 60–80 degrees C.

The crude high molecular weight polyanhydride copolymer was purified under nitrogen and precipitated in dry petroleum ether from dichloromethane solution. The solution was pressure filtered through a 0.2 micron filter and dripped into 600 ml of dry petroleum ether that was stirred using a mechanical stirrer. The resulting white fiber-like precipitate was then extracted with anhydrous ether for several hours at room temperature. Polymer analysis was done by melting point determination, molecular weight by GPC's and UV analysis which revealed a weight average molecular weight of 118,000 and an intrinsic viscosity of 0.92 dl/g.

EXAMPLE II

A 50:50 CPP:SA copolymer was prepared by mixing 2.0 grams of the CPP prepolymer with 1.15 grams of the sebacic acid prepolymer as prepared in Example I. The polymerization was carried out at 180 degrees C. under high vacuum (less than $10^{-2}$ mm Hg) for 90 minutes using the same procedure as in Example I. The resulting CPP:SA (50:50) copolymer had a weight average molecular weight of 38,200.

EXAMPLE III

A high molecular weight copolymer of 1.3 bis (p-carboxyphenoxy)propane:dodecanedioic acid was prepared using the pure isolated CPP prepolymer as in Example I. A dodecandioic acid prepolymer was prepared by adding 5.0 grams of dodecanedioic acid to 250 ml boiling acetic anhydride under dry argon and refluxed for 60 minutes. The excess acetic anhydride was removed by an evaporator at 60 degrees C. to yield a white solid which was dissolved in 20 ml dry toluene and allowed to crystallize overnight at 0 degrees C. The crystals were separated by filtration and extracted with 200 ml methyl ether and petroleum ether 1:1 mixture for 5 hours at room temperature. The pure crystals were then dried under vacuum over calcium chloride to yield 47 grams of prepolymer with a melting point of 76 degrees C.

A CPP:DD 20:80 polyanhydride copolymer was prepared by mixing 0.8 grams CPP prepolymer with 2.0 grams dodecanedioic acid prepolymer and polymerized at 180 degrees C. for 90 minutes under high vacuum (less than $10^{-2}$ mm Hg). The high molecular weight copolymer was purified as previously described and had a melting point of 70 to 76 degrees C., a weight average molecular weight of 125,900 and an intrinsic viscosity of 1.16 dl/g.

EXAMPLE IV

A 50:50 CPP:DD polyanhydride copolymer was prepared by mixing 1.0 grams of dodecanedioic acid prepolymer with 1.6 grams CPP prepolymer (as prepared in Example III) at 180 C for 90 minutes under high vacuum ($10^{-2}$ mm Hg) The resulting copolymer was purified as above and had a melting point of 158 to 160 degrees C., a weight average molecular weight of 44,800, a composition of CPP:DD (51:49) and an intrinsic viscosity of 0.76 dl/g.

EXAMPLE V

A high molecular weight polyanhydride of CPP:DD having a ratio of 65:35 was prepared by mixing 2.6 grams of CPP prepolymer with 0.88 grams of dodecanedioic acid prepolymer as prepared in Example I and polymerizing at 180 degrees C. for 90 minutes under high vacuum (less than $10^{-2}$ mm Hg). The purified copolymer had a melting point of 194 to 195 degrees C., a weight average molecular weight of 32,000, a composition of CPP:DD (64:36) and an intrinsic viscosity of 0.64 dl/g.

EXAMPLE VI

A high molecular weight copolymer of phenylene dipropionic acid and sebacic acid in a ratio of 20:80 was prepared using the sebacic acid prepolymer as prepared in Example I above. A phenylenedipropionic prepolymer was prepared by adding 60 grams of phenylenedipropionic acid to 500 ml boiling acidic anhydride under dry argon and refluxed for 60 minutes. The excess acetic anhydride is removed by an evaporator at 60 degrees C. to yield a white solid which was recrystallized from 30 ml toluene at 0 degrees C. The crystals are then extracted with 200 ml of a diethyl ether and petroleum ether (1:1) mixture for five hours at room temperature. The pure crystals are dried under vacuum under calcium chloride to yield 61 grams of prepolymer with a melting point of 74 to 75 degrees C.

The resulting 0.91 gram of PDP prepolymer is mixed with 3.28 grams of the sebacic acid prepolymer at 180 degrees C under high vacuum (less than $10^{-2}$ mm Hg) for 90 minutes. The resulting high molecular weight polyanhydride had a melting point of 56 to 59 degrees C., a weight average molecular weight of 84,920 and an intrinsic viscosity of 0.68 dl/g and a composition of PDP:SA (20:80).

EXAMPLE VII

A 50:50 copolymer of PDP:SA was prepared by mixing 1.14 grams of PDP prepolymer with 1.0 grams of SA prepolymer and polymerizing at 180 degrees C. under high vacuum (less than $10^{-2}$ mm Hg) for 90 minutes. The purified copolymer had a melting point of 75 to 77 degrees C., a weight average molecular weight of 58,900 and an intrinsic viscosity of 0.64 dl/g and a composition of PDP:SA (49:51).

EXAMPLE VIII

A 50:50 copolymer of PDP:CPP was prepared by mixing 1.14 grams of PDP prepolymer with 2.0 grams of CPP prepolymer (as prepared above) and polymerizing at 180 degrees C. under high vacuum (less than $10^{-2}$ mm Hg) for 90 minutes. The purified copolymer had a melting point of 158 to 160 degrees C, a weight average molecular weight of 34,400, and intrinsic viscosity of 0.65 dl/g and a composition of PDP:CPP (48:52).

EXAMPLE IX

A high molecular weight copolymer of CPP:PDP:SA in a ratio of 50:25:25 was prepared using the purified prepolymers as described above. 2.0 grams of CPP prepolymer was added to 0.57 grams of PDP prepolymer and 0.5 gram of SA prepolymer and polymerized at 180 degrees C. under high vacuum (less than $10^{-2}$ mm Hg) for 90 minutes. The resulting copolymer was purified as described above and had a melting point of 142 to 144 degrees C., a weight average molecular weight of 28,900, an intrinsic viscosity of 0.58 dl/g and a composition of CPP:PDP:SA (48:27:25).

Figure 2:
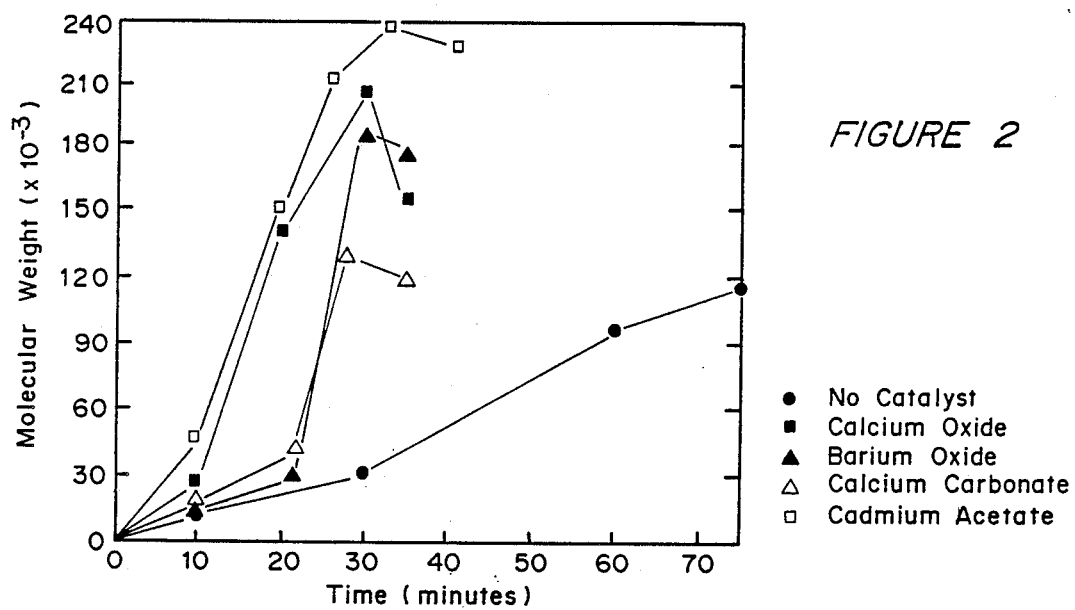
FIG. 2 is a graph of the molecular weight ($\times 10^3$) of CPP:SA copolymers polymerized by melt polycondensation in the presence of no catalyst or 2 mole % catalyst: calcium oxide, barium oxide, calcium carbonate and cadmium acetate, as a function of time of polymerization in minutes.

The weight average molecular weight of the copolymers can be significantly increased by including a catalysts with the prepolymers in the melt polymerization. Any catalyst used for transesterification, ring opening polymerization and related polymerizations are useful. In the preferred embodiments acid, base and coordination catalysts, such as $Cd(CH_3COO)_2$, earth metal oxides including CaO, BaO, $CaCO_3$, and $ZnEt_2H_2O$ are used. These catalyst were found to have a minor effect on the number average molecular weight. Table 1 compares the viscosity and weight average molecular weight for CPP:SA (20:80) polymers, melt polymerized at 180 degrees C. using various 2 mole percent coordination catalysts. Significantly higher molecular weights in shorter times were $Cd(CH_3COO)_2$, earth metal oxides, calcium carbonate and $ZnEt_2H_2O$. As can be seen in FIG. 2 the molecular weight of CPP:SA (20:80) increased up to 240,133 with a catalyst, in comparison to a weight average molecular weight of 116,800 without a catalyst. These catalysts are preferred since the reaction type is heterogenic, resulting in easy separation of the catalyst, which is a requirement for use of the copolymer in vivo or other medical applications.

TABLE 1

Melt Polymerization of CPP-SA (20:80)
Using Coordination Catalysts*

| Catalyst | polymerization time (min) | viscosity** [n] (dl/g) | molecular weight*** Mw |
|---|---|---|---|
| no catalyst | 90 | 0.92 | 116,800 |
| Barium oxide | 30 | 0.96 | 185,226 |
| Cadmium acetate | 31 | 1.15 | 240,133 |
| calcium oxide | 20 | 0.88 | 140,935 |
| calcium carbonate | 28 | 0.81 | 128,763 |
| ZnEt$_2$—H$_2$O (1:1) | 60 | 1.18 | 199,060 |

Figure 3:
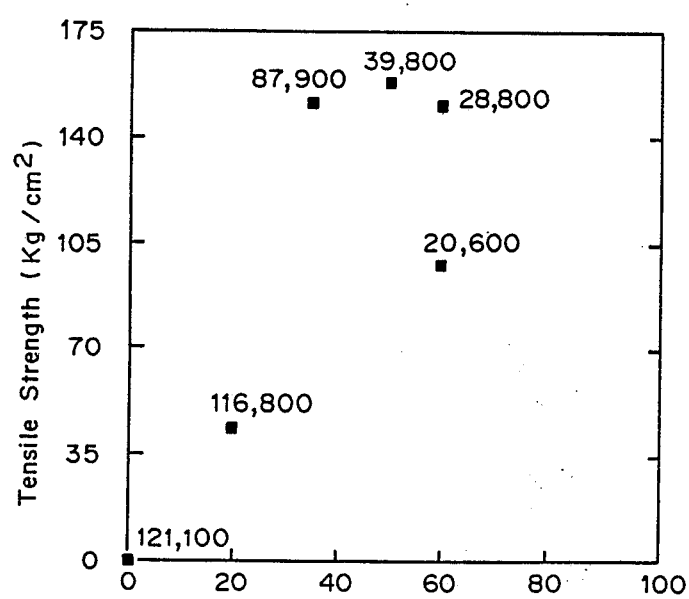
FIG. 3 is a graph of the tensil strength ($Kg/cm^2$) of poly(CPP:SA) films as a function of the percent CPP and molecular weight.

*2 mole %
**Chloroform, 23 degrees C.
***GPC - calibrated with polystyrene standards The molecular weights of CPP:SA (20:80) polymerized with 2 mole percent catalyst are depicted in FIG. 3 as a function of time and polymerization. Calcium oxide, barium oxide, calcium carbonate and cadmium acetate are used as the catalysts. The molecular weight and polymerization time for the polymerization of polyanhydrides carried out at 180 degrees C. with the catalyst cadmium acetate are listed in Table 2.

TABLE 2

Polymerization of polyanhydrides using cadmium acetate as catalyst

| Polymer | polymerization time (min) | Mw |
|---|---|---|
| P(IPh:SA) (20:80) | 40 | 178,100 |
| P(IPh:SA) (50:50) | 35 | 87,850 |
| P(CPP:DD) (20:80) | 35 | 184,900 |
| P(CPP:DD) (50:50) | 40 | 61,050 |
| DD | 60 | 134,200 |
| SA | 60 | 138,500 |

These results demonstrate that high molecular weight polyanhydrides can be synthesized only when critical parameters are observed. In the above examples the conditions which must be optimized to achieve the high molecular weights include the reaction time, the reaction temperature, high vacuum and the use of purified prepolymers. The molecular weight of these copolymers can further be significantly increased by including a catalyst, preferably a coordination catalyst, an earth metal oxide, calcium carbonate or a complex of ZnEt hydroxylated compound.

These high molecular weight polyanhydrides have many useful applications in the biomedical area including the manufacture of sutures, protective coverings, and as absorbable bone replacements. The high molecular weight polyanhydrides are particularly useful for controlled drug delivery devices. The controlled drug delivery devices according to the present invention are suitable for subcutaneous implantation to deliver a suitable drug, implanting in the fluid of the eye for treatment of glaucoma, subdermal implant for delivering contraceptive steroids, and implanting in the mouth for delivering fluoride. The novel drug delivery devices are also suitable for transdermal drug delivery, for example in the treatment of motion sickness, immunizations and treatment of angina.

Any biologically active substance can be utilized in conjunction with the polyanhydride so long as it is capable of being intimately admixed with the polyanhydride and subsequently formed into a desired shape without affecting the bioavailability of the drug. The active substance can be a protein or it can be nonproteinaceous; it can be a macromolecule $$\left(\frac{M.W. > 2}{1000} \text{ daltons}\right)$$

or a relatively low molecular weight molecule; and it can be soluble or insoluble in water. Examples of suitable active substances are interferon, anti-angiogenesis factors, antibodies, antigens, polysaccharides, growth factors, hormones including insulin, glucogen, parathyroid and pituitary hormones, calcitonin, vasopressin, renin, prolactin, growth hormones, thyroid stimulating hormone, corticotrophin, follicle stimulating hormone, luteinizing hormone, and chorionic gonadotropins; enzymes, including soybean trypsin inhibitor, lysozyme, catalase, tumor angiogenesis factor, cartilage factor, transferases, hydrolases, lysases, isomerases, proteases, ligases and oxidoreductases such as esterases, phophatases, glycosidases, and peptidases; enzyme inhibitors such as leupeptin, antipain, chymostatin and pepstatin; and drugs such as steroids, anti-cancer drugs or antibiotics.

The improved effectiveness and desirable characteristics of the novel controlled drug delivery devices are due primarily to the employment of the above high molelcular weight polyanhydrides previously described rather than the low molecular weight polyanhydrides used in the prior art methods. The high molecular weight polyanhydrides in combination with the novel method of forming the controlled drug release devices result in a device which exhibits zero order release of the drug, a polymer which degrades at a constant rate and a device which is not subject to the drug/polymer interactions commonly encountered in the prior art devices.

A significant advantage of using these high molecular weight polyanhydrides is that they exhibit superior film forming qualities compared to the low molecular weight polyanhydrides of the prior art. These film forming characteristics permit solvent casting of the polymer drug matrix at room temperature. By being able to form the bioerodible devices at room temperature, the undesirable interaction between the polymer and the drug and degradation of the polymer or drug is avoided which commonly occurs in compression and melt casting techniques.

The superior film forming qualities of the high molecular weight polyanhydrides is in part attributed to the high intrinsic viscosity. The prior art polyanhydrides which had molecular weight approaching 20,000 had relatively low intrinsic viscosities (below 0.3 dl/g) while those polymers having the greater viscosities had comparatively low molecular weights. It has been found that the superior film forming qualities of the high molecular weight polyanhydrides result from both the high molecular weight (greater than 20,000) and the greater intrinsic viscosity (greater than 0.3 dl/g).

In the preferred embodiment the bioerodible controlled drug release devices are prepared by a solvent casting technique. This technique dissolves the high molecular weight polyanhydride in powder form in a 20 percent solution of 1.0 gram of polymer in methylene chloride which is then placed in a 20 ml scintillation vial. The substance to be added to the polymeric matrix, for example a drug, is then placed in the solution at the desired polymer to drug ratio. The solution is then placed in a 0 degree freezer for 15 minutes during which time a heavy glass mold is prechilled on a metal platform immersed in a water/liquid nitrogen bath. At the time of molding, the viscous polymer or polymer/drug solution is mixed and poured into the glass mold where it will freeze immediately. The resulting film is cut into uniform disks which are then dried under vacuum to remove all traces of solvent. The resulting bioerodible devices are translucent, flexible and shelf stable.

The improved film forming characteristics of the high molecular weight polyanhydrides are further related to the tensil strength of the polymer. As demonstrated in FIG. 3 the tensil strength of the polyanhydride film made of CPP polymers is a function of the molecular weight and as a function of the percent of CPP present in the copolymer. As the percent of CPP is increased in the copolymer and/or the molecular weight is increased the tensil strength is also increased. These studies demonstrate that the tensil strength of the high molecular weight polyanhydride copolymers are proportional to the percent of aromatic repeating units in the copolymer. As indicated in the graph of FIG. 3 the copolymer having 20% CPP and a molecular weight 116,800 produces in a film having a suitable tensil strength of 40–45 kg/cm$^2$. Further studies have demonstrated that as low as 5% aromatic units in the copolymer chain produce beneficial film forming qualities necessary for solvent casting techniques.

Figure 16:
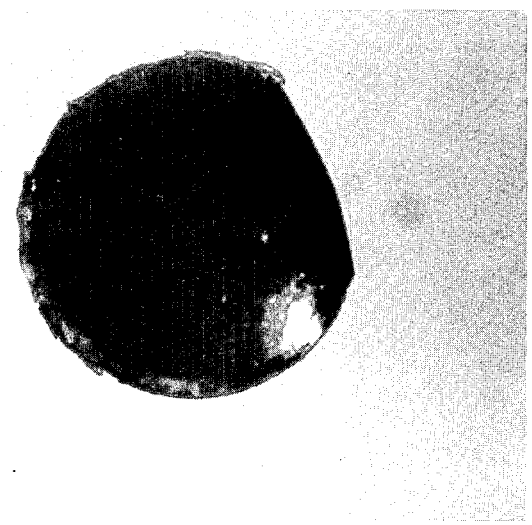
FIG. 16 is a photograph of a solvent cast disk of the high molecular weight polyanhydride copolymer matrix, magnified 20×.
Figure 17:
FIG. 17 is a photograph of normal subcutaneous tissue of a rat with dermis, subcutaneous fat, subcutaneous muscle and subcutaneous connective tissue magnified 40×.
Figure 18:
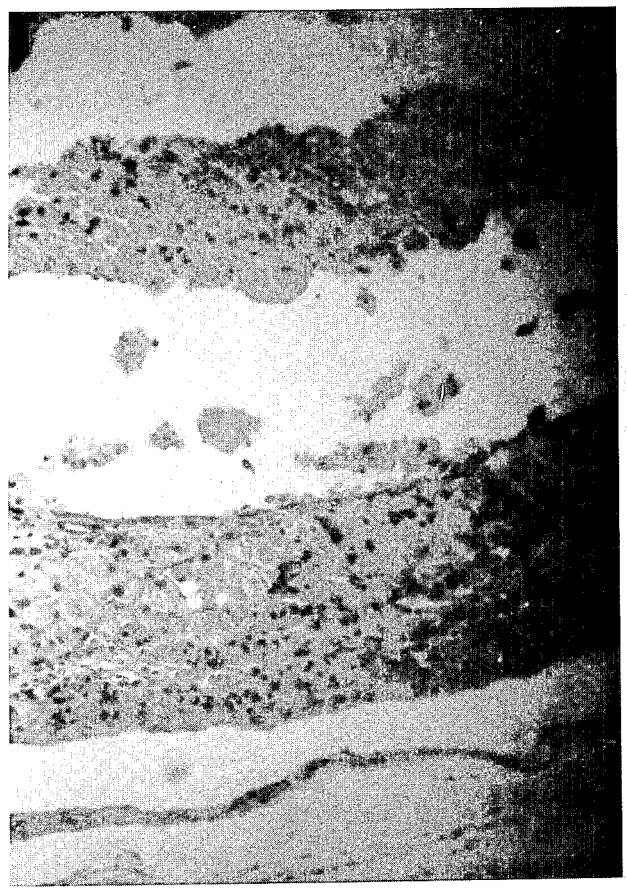
FIG. 18 is a photograph of subcutaneous tissue of a rat after implantation with 1 high molecular weight polyanhydride copolymer disk, magnified 100×.

The high molecular weight polyanhydrides also have improved biocompatibility compared to the prior art low molecular weight polyanhydrides thereby contributing to their utility in biomedical applications. The improved biocompatibility is apparent by comparing normal subcutaneous rat tissue as shown in FIG. 17 with FIG. 18 showing the subcutaneous rat tissue after implantation with 1 disk of the high molecular weight polyanhydride revealing the presence of residual polymer and macrophages. The polyanhydride disk in the above and following examples as shown in FIG. 16 was a 200 mg wafer which when implanted into a rat represents 267 mg times the anticipated human dose on the basis of weight of polymer to body weight.

Figure 19:
FIG. 19 is a photograph of subcutaneous tissue of a rat after implantation with 3 high molecular weight polyanhydride copolymer disks, magnified 16×.

A sample of subcutaneous rat tissue implanted with 3 high molecular weight polyanhydride disks is shown in FIG. 19. As can be seen, residual polymer appears in the upper portion of the photograph. Some of the polymer remaining is surrounded by a zone of macrophages and connective tissue.

Figure 20:
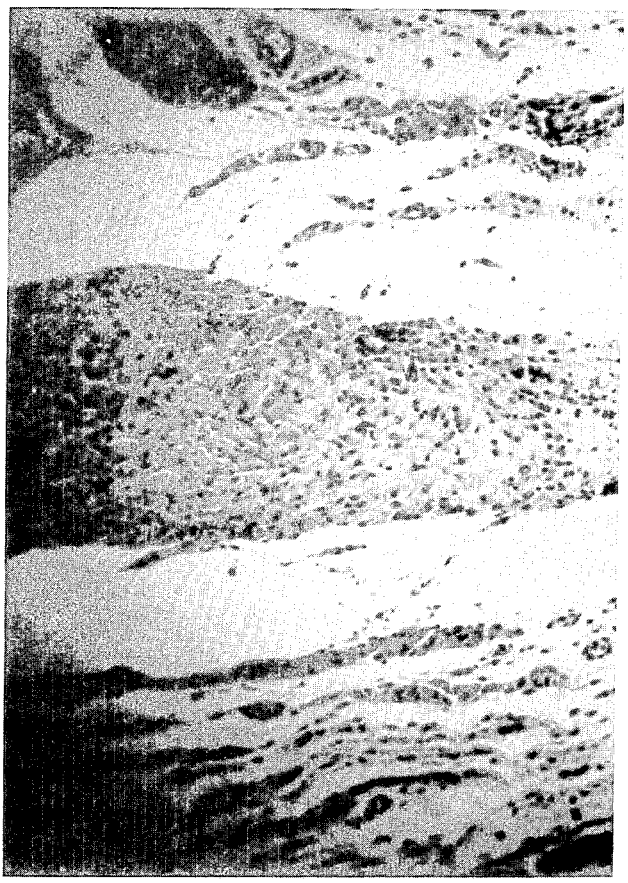
FIG. 20 is a photograph of subcutaneous tissue of a rat after implantation 1 high molecular weight polyanhydride copolymer disk magnified 100×.
Figure 21:
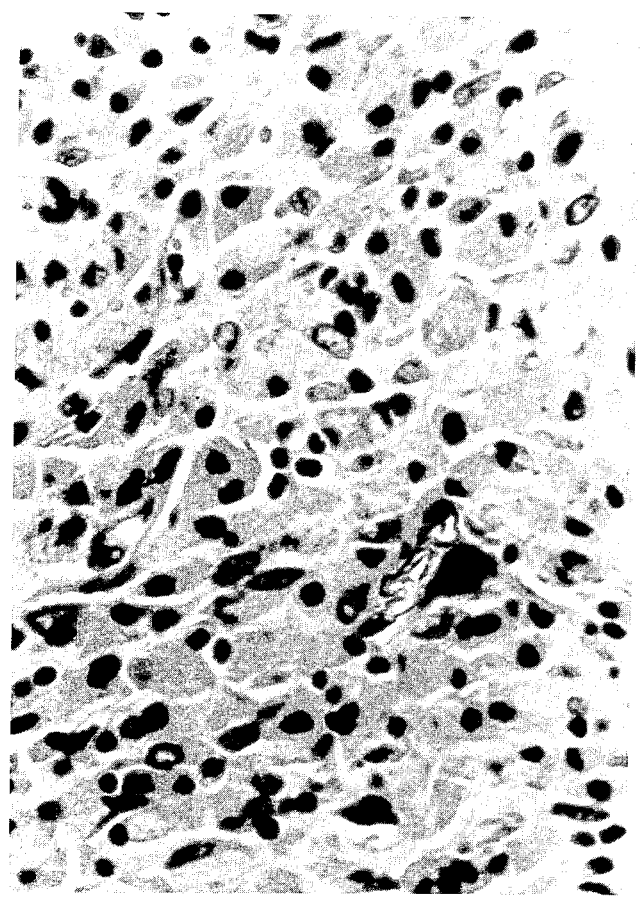
FIG. 21 is a photograph of subcutaneous tissue of a rat after implantation with 1 high molecular weight polyanhydride copolymer disk, magnified 400×.
Figure 22:
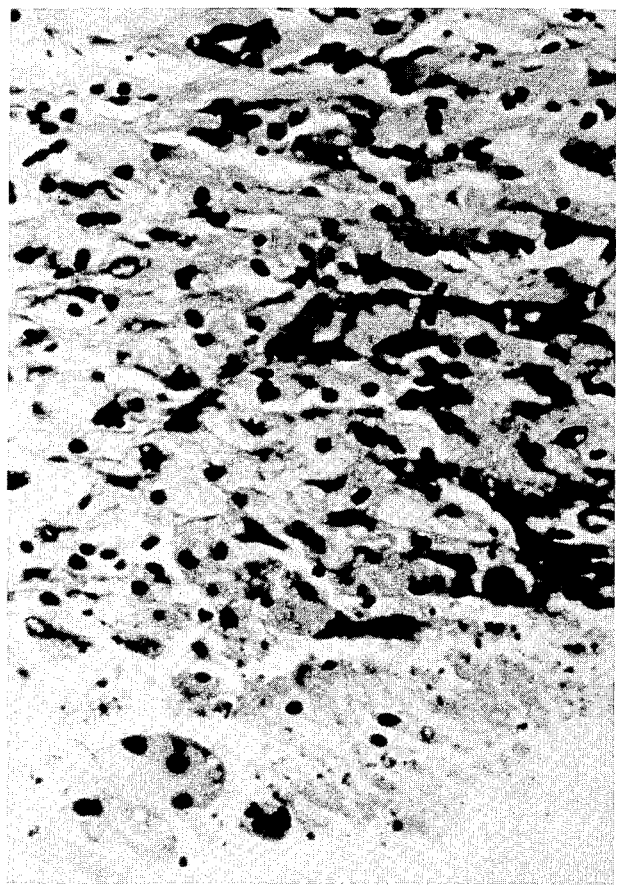
FIG. 22 is a photograph of subcutaneous tissue of a rat after implantation with 3 high molecular weight polyanhydride copolymer disks, magnified 250×.

FIG. 20 shows the subcutaneous tissue of a rat implanted with 1 disk of the high molecular weight polyanhydride after the polymer has completely eroded. The resulting tissue in the vicinity of the polymer consists of fibroblasts and macrophages. Additional testing was carried out to further determine the effects of the high molecular weight polyanhydrides subcutaneously implanted in tissue. For example, as can be seen in FIG. 21 the subcutaneous tissue of a rat shows no residual polymer and the tissue consisting essentially of fibroblasts, micraphages and an occasional lymphocyte. FIG. 22 shows the subcutaneous tissue of a rat after implantation with 3 high molecular weight disks. As can be seen some residual polymer is present in the lower portion of the photograph. The tissue consists essentially of fibroblasts, macrophages and an occasional lymphocyte.

Figure 23:
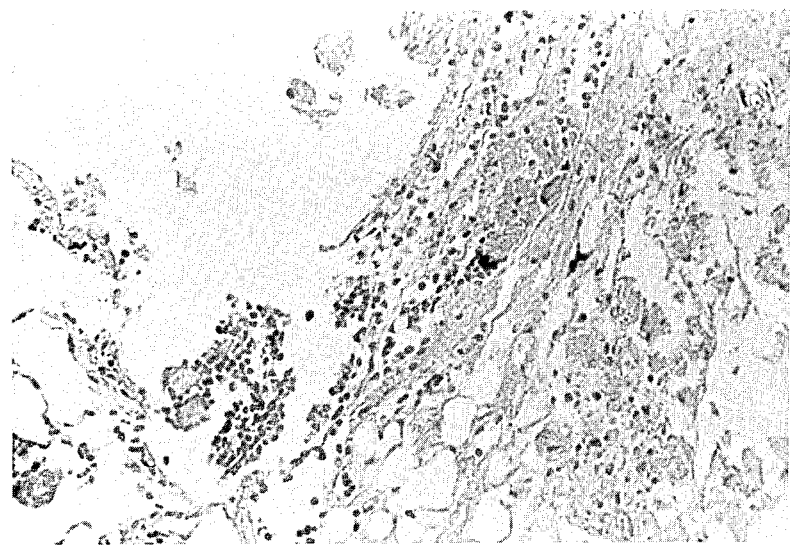
FIG. 23 is a photograph of a first sample of subcutaneous tissue of a rat after implantation with 1 low molecular weight polyanhydride copolymer disk of the prior art, magnified 64×.

The low molecular weight polyanhydrides of the prior art were also examined to demonstrate the improved biocompatibility of the high molecular weight polymers. Referring to FIG. 23 the subcutaneous tissue of a rat implanted with 1 low molecular weight polyanhydride is shown. Throughout this sample residual polymer can be seen. The tissue after erosion of the polymer consisted of macrophages, lymphocytes, polymorphonuclear cells, foreign body giant cells and fibroblasts. In addition much of the general architecture of the subcutaneous tissue is no longer present.

Figure 24:
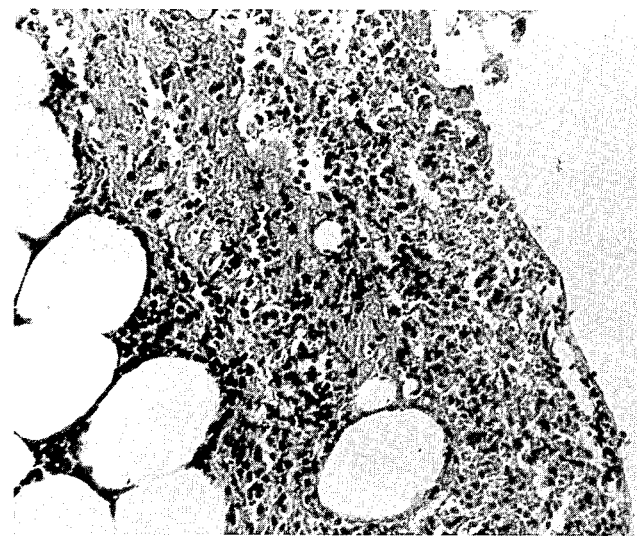
FIG. 24 is a photograph of a second sample of subcutaneous tissue of a rat after implantation with 1 low molecular weight polyanhydride disk of the prior art, magnified 64×.
Figure 25:
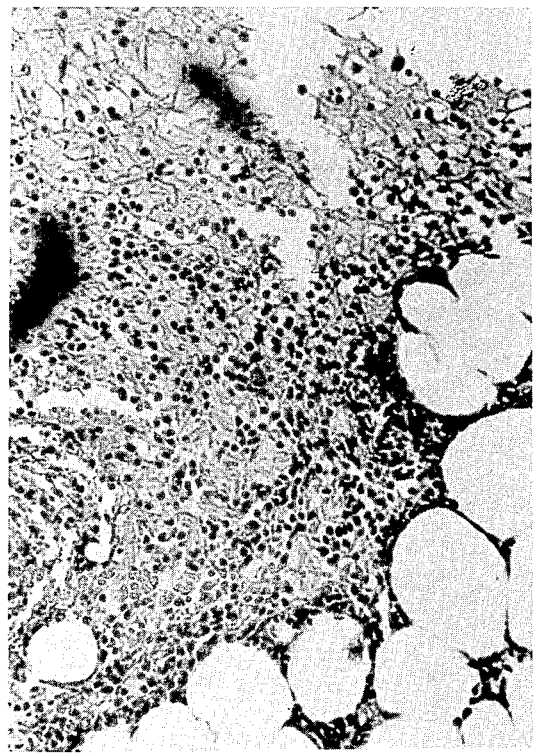
FIG. 25 is a photograph of a third sample of subcutaneous tissue of a rat after implantation with 1 low molecular weight polyanhydride disk of the prior art magnified 64×.

Second and third examples of subcutaneous tissue of a rat implanted with 1 disk of the low molecular weight polyanhydrides can be seen in FIG. 24 and FIG. 25 respectively. In these examples no residual polymer is present. The tissue after polymer erosion was hypercellular consisting of lymphocytes, polymorphonuclear cells, macrophages and fibroblasts.

Figure 26:
FIG. 26 is a fourth sample of subcutaneous tissue of a rat after implantation with 1 low molecular polyanhydride disk of the prior art, magnified 40×.

The prior art low molecular weight polyanhydrides generally tended to cause destruction of the underlying tissue as can be seen in a fourth sample as shown in FIG. 26. This destruction of tissue resulted from the implantation and erosion of low molecular weight polyanhydrides in the subcutaneous tissue of a rat.

The above results demonstrate the high molecular weight polyanhydrides tended to preserve the local surrounding tissue while the prior art lower molecular weight polyanhydrides exhibited hypercellular tissue and destruction of the local surrounding tissue. Additionally the lower molecular weight polyahydrides produced a response which was primarily lymphocytic and resulted in destructive polymorphonuclear cells.

Conversely the novel high molecular weight polyanhydrides induced a response which was via macrophages without the production of any significant amounts of polymorphonuclear cells.

These results reveal a considerably milder response to the tissue with the implantation of high molecular weight polyanhydride copolymers than the response to the prior art low molecular weight polyanhydrides. The strong lymphocytic and polymorphonuclear response of the low molecular weight polyanhydrides in combination with the tissue destruction which are not present with the implantation of the high molecular weight polyanhydrides demonstrate improved benefits of using the high molecular weight polyanhydrides for controlled release of drugs.

Figure 4:
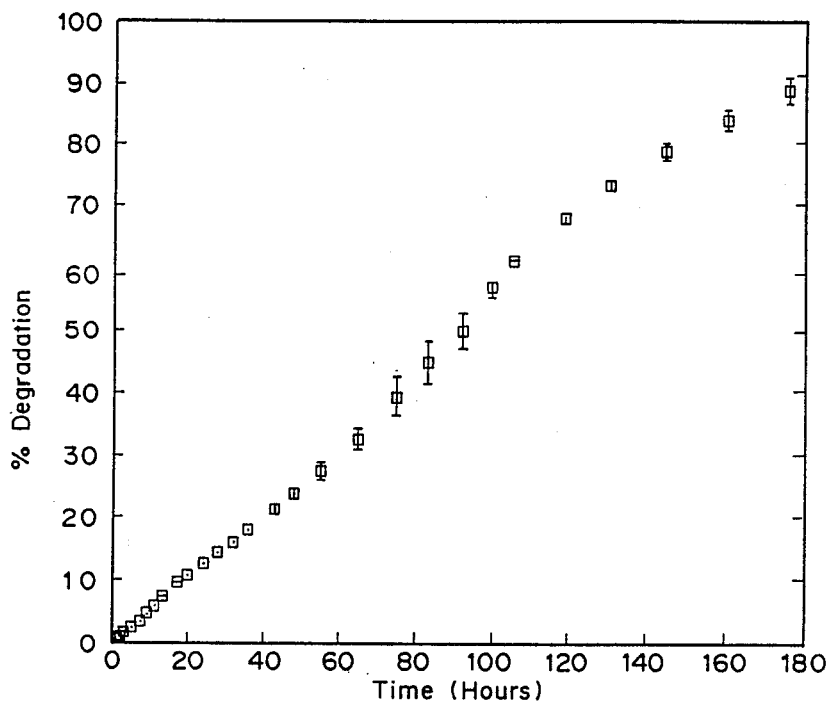
FIG. 4 is a graph of the degradation of low molecular weight CPP:SA (9:91) as a function of time in minutes.
Figure 5:
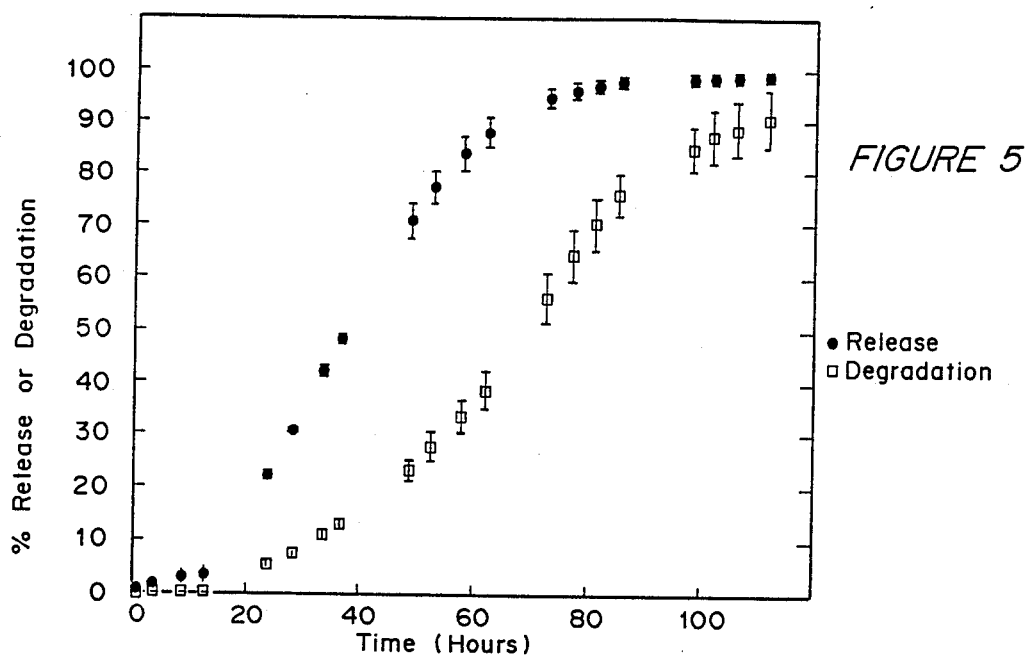
FIG. 5 is a graph of the rate of degradation of high molecular weight CPP:SA (30:70) and the rate of release of colchicine as a function of time in hours.

The bioerodible controlled drug release devices formed from high molecular weight polyanhydrides exhibit superior degradation characteristics. Referring to FIG. 4 the degradation rate of a low molecular weight (under 20,000) CPP:SA (9:91) copolymer containing 1 percent p-nitroanaline is shown. This graph demonstrates that for low molecular weight polyanhydrides no induction period for degradation occurs. In comparison with FIG. 5 a high molecular weight copolymer of CPP:SA (30:70) containing 5 percent colchicine demonstrates a considerable induction period prior to initial polymer degradation and drug release. This induction period is attributed primarily to the increased hydrophobicity of high molecular weight polyanhydrides.

Figure 6:
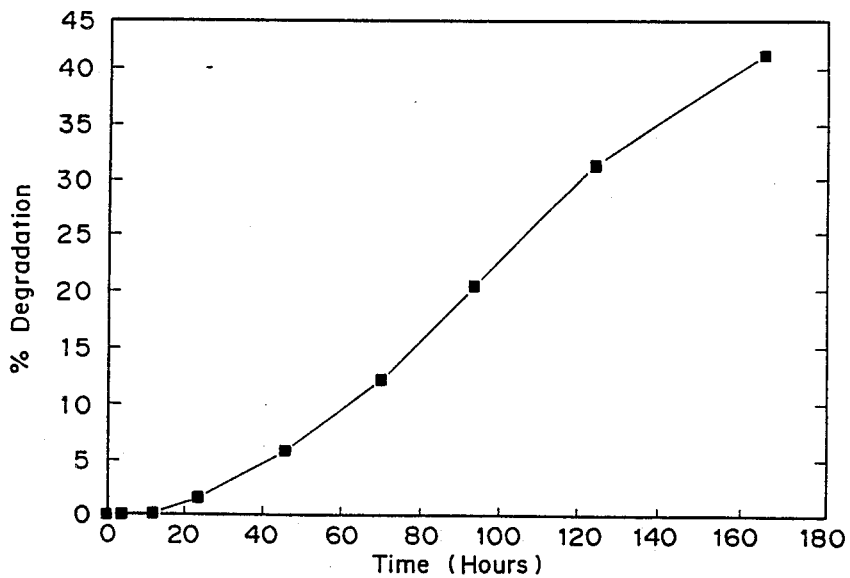
FIG. 6 is a graph of the rate of degradation of high molecular weight CPP:SA (65:35) as a function of time in hours.

The high molecular weight polyanhydrides have fewer hydrophobic polymer chain end groups which lead to a more hydrophobic polymer and to a polymeric matrix of greater density. In addition, the polymeric matrices formed from the high molecular weight polyanhydrides have been found to possess a greater density when prepared by solvent casting techniques. The higher density of the polymeric matrix also serves to increase the hydrophobicity of the resulting matrix. This increased hydrophobicity compared to the lower molecular weight polyanhydrides of the prior art translate into an induction period before the polymer surface is sufficiently wetted for degradation to occur. Further examples comparing the induction period of the high molecular weight polyanhydrides to the low molecular weight polyanhydrides are disclosed in FIGS. 6 (high molecular weight) and 7 (low molecular weight).

Figure 7:
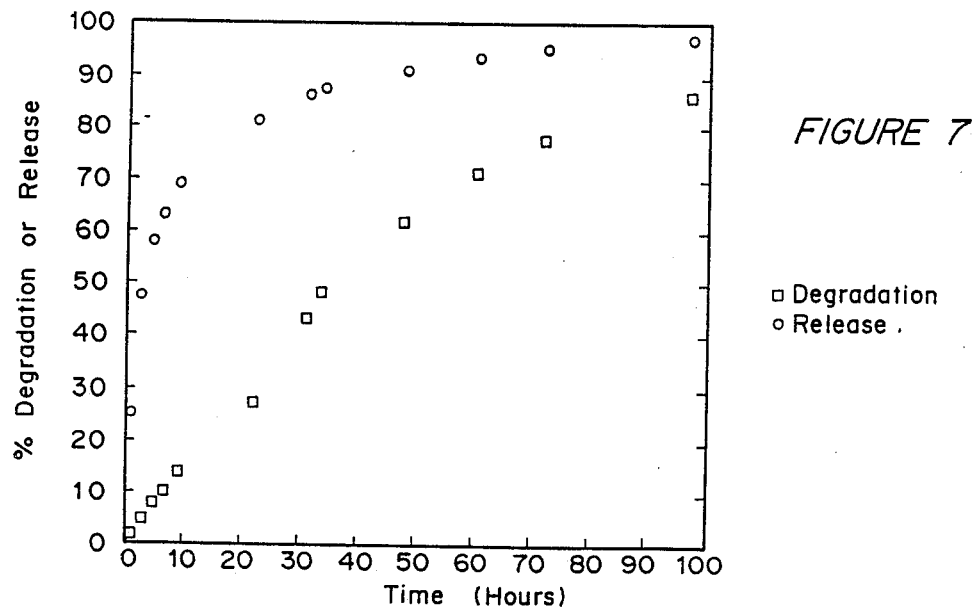
FIG. 7 is a graph of the rate of degradation and release of p-nitroaniline from low molecular weight CPP:SA (9:91) as a function of time.
Figure 8:
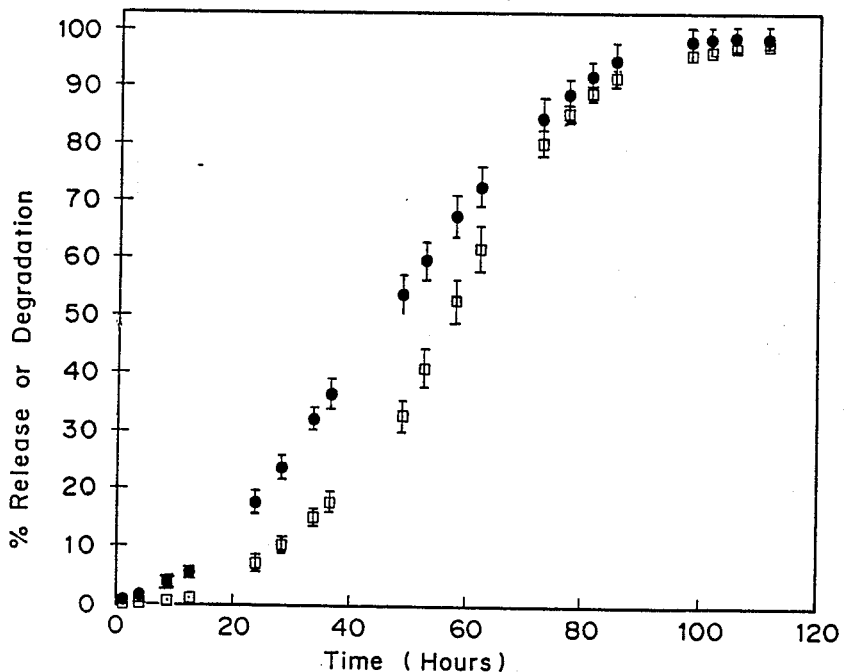
FIG. 8 is a graph of the rate of degradation and release of p-nitroaniline from high molecular weight CPP:SA (30:70) as a function of time.

Further advantages of using the high molecular weight polyanhydrides for controlled drug release devices can be seen in the kinetics of the release of drugs. Referring to FIG. 8 a comparison of the rate of release of the drug to the rate of degradation of a high molecular weight CPP:SA (30:70) copolymer indicates the rate of release of the drug and degradation of the polymer occuring at nearly the same rate. In comparison with the low molecular weight polyanhydride of CPP:SA (9:91) as disclosed in FIG. 7 the rate of release of the drug far exceeds the rate of degradation of the polymer.

Figure 9:
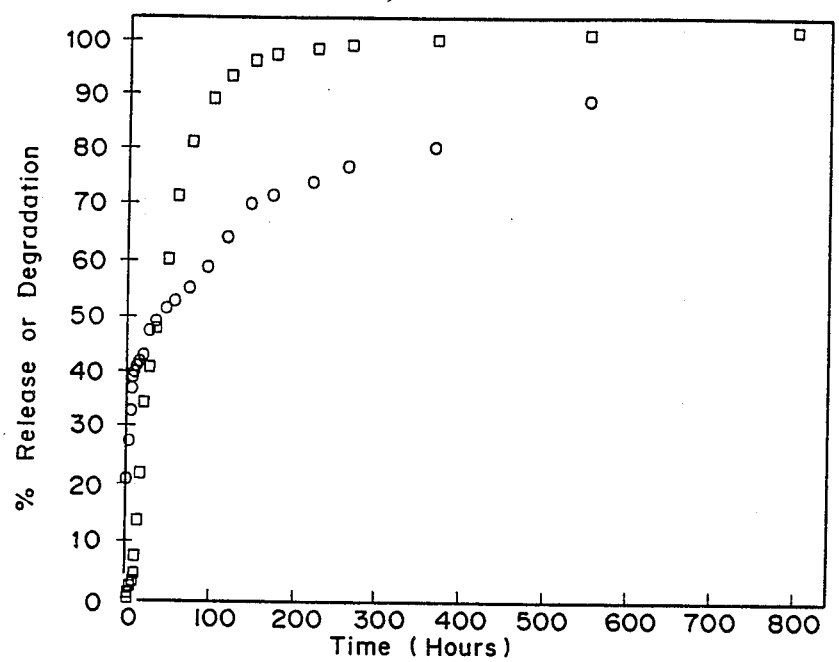
FIG. 9 is a graph of the rate of degradation and rate of release of B-galactosidase from low molecular weight CPP:SA (9:91) as a function of time.
Figure 10:
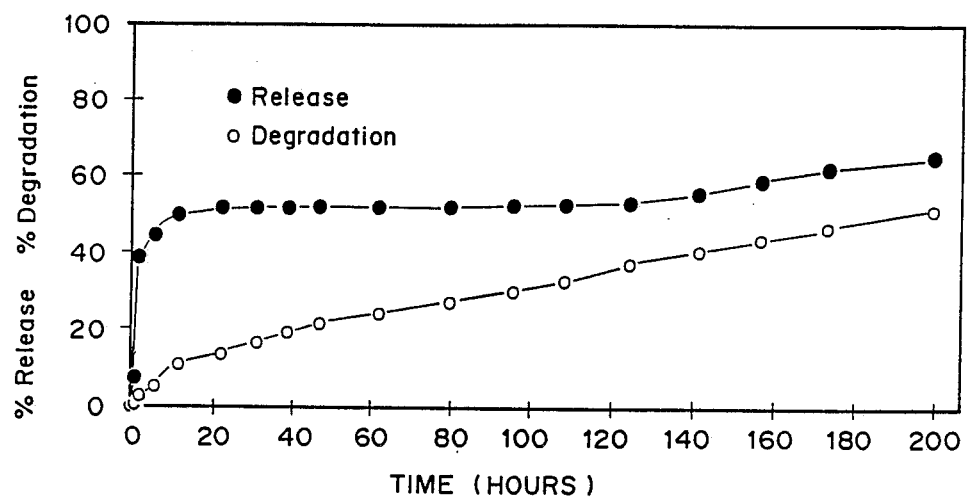
FIG. 10 is a graph of the degradation and release of catalase from high molecular weight CPP:SA (30:70) as a function of time.

The controlled drug delivery devices formed from the high molecular weight polyanhydrides have further been shown to exhibit improved release rates of high molecular weight (macromolecules) drugs. As shown in FIG. 9 a low molecular weight copolymer of CPP:SA (9:99) forms into a matrix containing 5 percent beta galacosidase shows a rate of release of the high molelcular weight drug much lower than the weight of degradation of the polymer. In comparison, a polymeric matrix formed from the high molecular weight polyanhydrides results in a rate of release of the high molecular weight drug to be greater than the rate of release from low molecular weight polymers as demonstrated in FIG. 10. This difference between the rate of degradation and rate of release of high molecular weight drug is believed to be due to the fabrication techniques required for low molecular weight polyanhydrides.

In bioerodible controlled drug release devices it is desirable to have the rate of release of the drug correspond as closely as possible to the rate of degradation of the polymer. By correlating these rates it is possible to have the supply of drug depleted simultaneously with the complete erosion of the polyanhydride. Similarly, it is possible to avoid having an excess concentration of the drug released at the end of life-span of the polymer if the polyanhydride erodes faster than the release of the drug.

Polymeric matrices prepared from high molecular weight polyanhydrides further have the advantage of being able to preserve the bioactivity of polypeptides when implanted in vivo unlike the low molecular weight polyanhydrides. This is most likely due to the fact that the interaction between the polypeptides and the polymer caused an inadequate release of the macromolecules and/or reduced activity of the macromolecules.

The following examples demonstrate the use of high molecular weight polyanhydrides synthesized according to the method of the present invention.

EXAMPLE X

Figure 11:
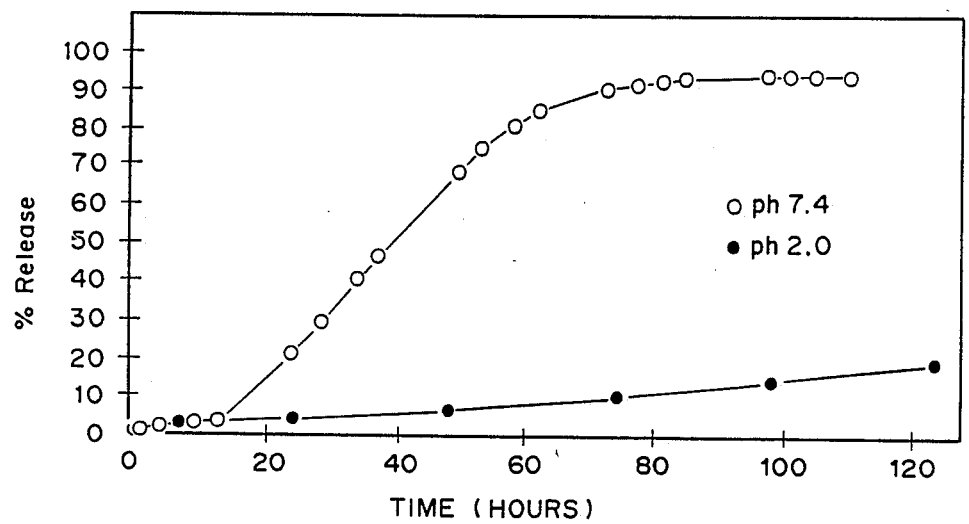
FIG. 11 is a graph of the degradation and release of colchine from high molecular weight CPP:SA (30:70) at pH 7.4 and pH 2.0.

In vitro release of colchicine from a polyCPP:SA (30:70) film of 5 percent colchincine loading The in vitro release rate for a representative drug, colchicine (400 mw), from a polyCPP:SA (30:70) film is shown in FIG. 11 as the percent release over time (hr) at 37 degrees C. in buffered solutions having a pH of 2.0 and 7.4. The one mm thick fil was formed by solvent casting the 5 percent colchicine - polyCPP:SA (30:70) solution mixture.

The results demonstrate that a controlled release occurs over a period of at least six days at pH 7.4 due to surface erosion of the polymer. Since the polymer is relatively stable at pH 2.0, there is no leaching of the colchicine out of the film due to other factors.

EXAMPLE XI

Figure 12:
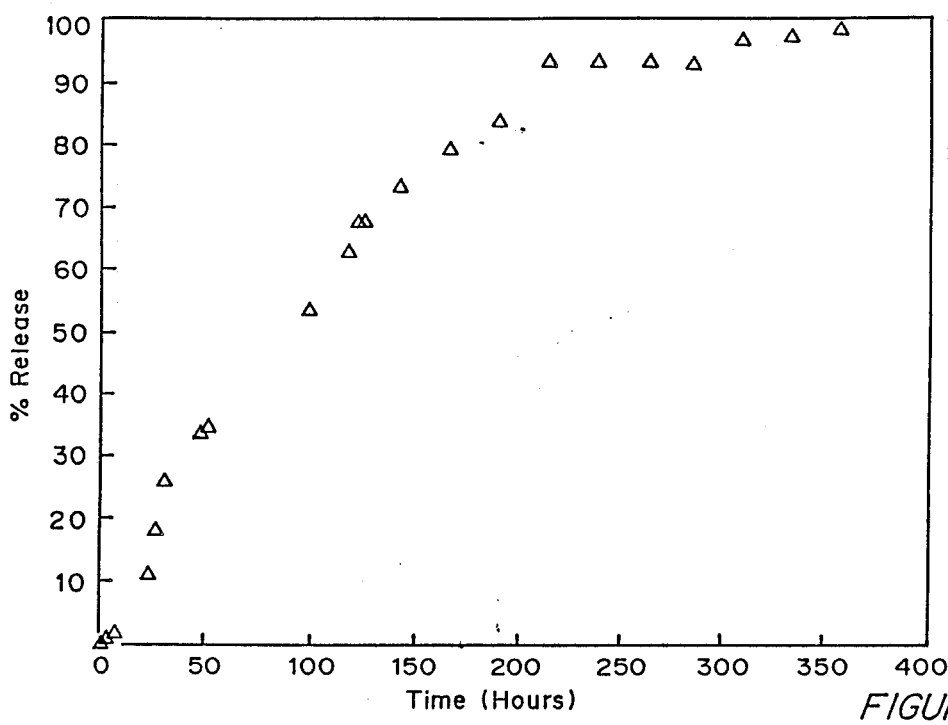
FIG. 12 is a graph of the percent of insulin released in vitro over time from 300 micron CPP:SA (20:80) microspheres in pH 7.4 buffer at 37 degrees C.

In vivo release rate of insulin, a polypeptide hormone of approximately 6000 molecular weight, from 300 micron polyCPP:SA (20:80) microspheres having a weight average molecular weight of 92,000 is shown in FIG. 12. The percent release of insulin into 0.1M phosphate buffer pH 7.4 at 37 degrees C. clearly establishes that zero order release is occurring over a period of approximately two weeks.

EXAMPLE XII

Figure 13:
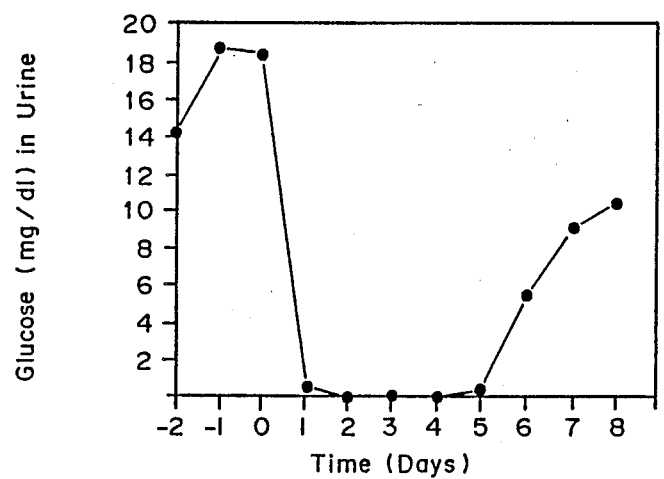
FIG. 13 is a graph of glucose (mg/dl) in urine over time (days) demonstrating effect of in vivo release of insulin in rats from 300 micron microspheres formed of poly CPP:SA (20:80) of 5% insulin.
Figure 14:
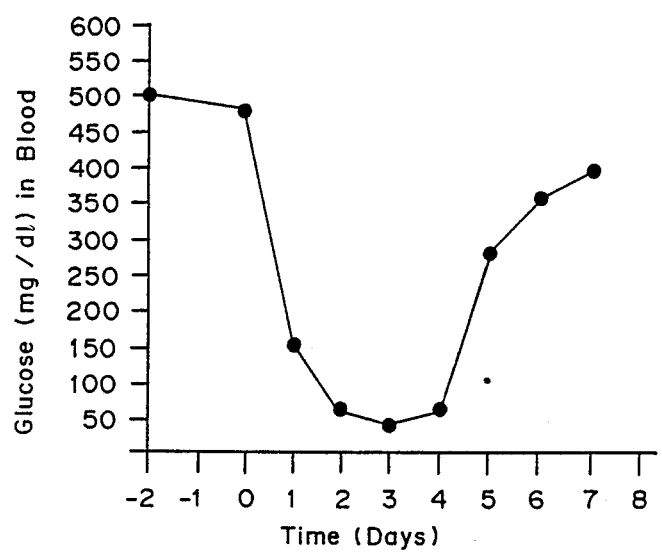
FIG. 14 is a graph of glucose (mg/dl) in blood over time (days) demonstrating the effect of in vivo release in rats of insulin for 300 micron microspheres formed of poly CPP:SA (20:80) of 5% insulin.

In vivo release of insulin in rats from 300 micron polyCPP:SA (20:80) microcapsules The effectiveness of insulin release in vivo in rats (average 200 g) from 300 micron polyCPP:SA (20:80) microspheres of 5 percent insulin loading is demonstrated in FIGS. 13 and 14. FIG. 13 is a graph of glucose (mg/dl) in urine over eight days. FIG. 14 is a graph of glucose (mg/dl) in blood over eight days. The insulin is released over a period of several days, with an effectiveness of four to five days at this loading in microspheres of this size and composition. The microspheres totally disappear after seven days.

The polyCPP:SA (20:80) polymers forming injectible microspheres of 300 microns have a molecular weight of 92,000. PolyCPP:SA (20:80) polymers formed using the prior art methods have a molecular weight of 12,000. Although not directly comparable, larger non-injectible size microspheres formed of the low molecular weight polyCPP:SA (20:80) of approximately 800 microns in diameter, of 5 percent insulin loading are required to obtain an effective release over a period of three days.

EXAMPLE XIII

Figure 15:
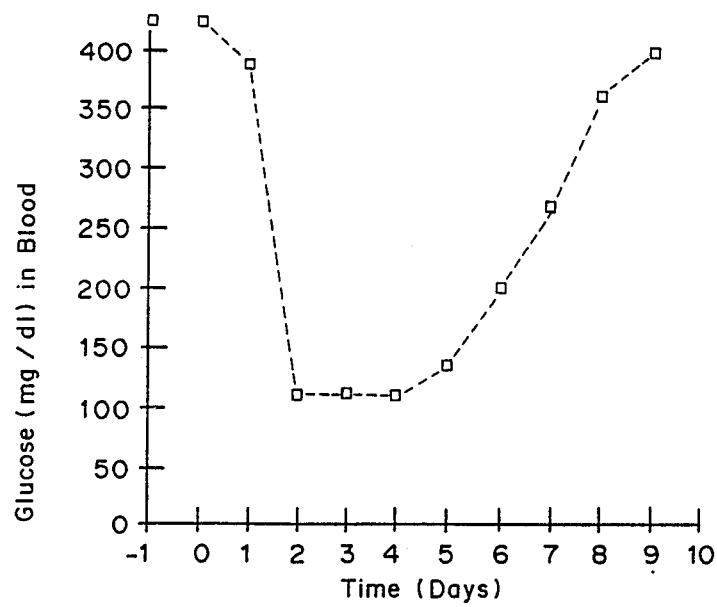
FIG. 15 is a graph of glucose (mg/dl) in blood over time (days) demonstrating the effect of in vivo insulin release in rats from a 0.5 mm poly CPP:SA (20:80) film of 5% insulin.

In vivo thick release of insulin in rats from a 0.5 mm thick poly-CPP:SA (20:80) film FIG. 15 shows the effectiveness of in vivo insulin release in rats over a period of several days from a polyCPP:SA (20:80) film of 5 percent insulin loading. The 0.5 mm thick film is prepared by suspending the insulin in the polymer dissolved in chloroform and casting. After removal of the solvent, the 200 mg film is surgically implanted under the skin of the rats (200 g average).

Release of the insulin from the films is effective in controlling blood glucose levels for approximately five days, slightly longer than release from the 300 micron microspheres of 5 percent insulin loading of Example 12. However, films have an even more important advantage over the injectable microspheres in that they may be surgically removed if there is a problem with the drug being released. Due to their particular nature and scattering, removal of microspheres is extremely difficult.

The detailed description of the invention is provided primarily for purposes of illustrating the preferred embodiment of the invention. It will be recognized by those skilled in the art that the preferred embodiment is not intended to limit the present invention to the particular structures and methods of the preferred embodiment as set forth above as they may be readily modified by those skilled in the art. It will be further apparent to those skilled in the art that numerous other modifications not mentioned herein can still be made without departing from the spirit and scope of the invention as claimed in the following claims.

What is claimed is:

1. A bioerodible controlled drug release device comprising a homogeneous polymeric matrix of:
   (a) an effective amount of at least one biologically active substance, and;
   (b) a high molecular weight hydrophobic polyanhydride copolymer having a weight average molecular weight greater than 20,000 and an intrinsic viscosity greater than 0.3 dl/in chloroform at 23° C., said polyanhydride produced from at least one dicarboxylic acid selected from the group consisting of:
aliphatic dicarboxylic acids having the formula:

aromatic dicarboxylic acids having the formula:

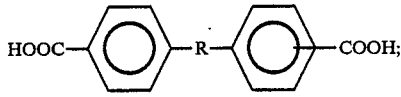

aromatic dicarboxylic acids having the formula:

aliphatic-aromatic dicarboxylic acids having the formula:

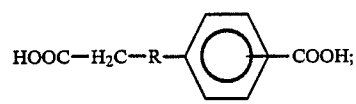

aromatic and aliphatic heterocyclic dicarboxylic acids having the formula:

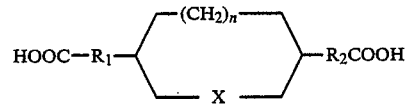

wherein
X is selected from the group consisting of oxygen, nitrogen, and sulfur, and
n is an integer between 1 and 3; and
aromatic and aliphatic heterocyclic dicarboxylic acids of the above formula in combination with at least one dicarboxylic acid selected from the group consisting of aliphatic dicarboxylic acids, aromatic-aliphatic dicarboxylic acids, and aromatic dicarboxylic acids having more than one phenyl group;
wherein the R groups are divalent organic radical groups.

2. The bioerodible controlled drug release device of claim 1 wherein said hydrophobic polyanhydride copolymer is synthesized by the steps of
   (a) selecting at least one essentially pure prepolymer from at least one essentially pure dicarboxylic acid reacted with acetic anhydride
   (b) polymerizing said prepolymer under a predetermined temperature, vacuum and for a length of time whereby the resulting polyanhydride has a molecular weight in excess of 20,000 and an intrinsic viscosity greater than 0.3 dl/g in an inorganic solvent at room temperature.

3. The bioerodible controlled drug release device of claim 2 wherein said predetermined vacuum of said polymerization step is at least $10^{-2}$ mm Hg.

4. The bioerodible controlled drug release device of claim 3 wherein said polymerization step is carried out in the presence of a catalyst.

5. The bioerodible controlled drug release device of claim 4 wherein said catalyst is selected from the group comprising alkaline earth metal oxides, calcium carbonate, coordination complexes of diethylzinc and hydroxylated compounds or $Cd(CH_3COO)_2$.

6. The bioerodible controlled drug release device of claim 1 wherein said high molecular weight hydrophobic polyanhydride has a molecular weight between 20,000 and 240,000 and has an intrinsic viscosity between 0.3 dl/g and 1.18 dl/g in chloroform at 23° C.

7. The bioerodible controlled drug release device of claim 1 wherein said high molecular weight hydrophobic polyanhydride is synthesized from a dicarboxylic acid selected from the group consisting of sebacic acid, bis(p-carboxyphenoxy) alkanes, isophthalic acid, dodecanedioic acid, hydroquinone-O,O'-diacetic acid, 1,4-bis(carboxymethyl) benzene, 2,2-bis(4-carboxyphenyl) propane, terephthalic acid, 1,4 phenylene dipropionic acid, bis(4-carboxyphenyl) alkanes and cyclohexane dicarboxylic acids.

8. The bioerodible controlled drug release device of claim 1 wherein said homogeneous matrix is prepared by the steps of
   (a) dissolving said hydrophobic polyanhydride in a suitable solvent to form a solution;
   (b) combining to the solution said biologically active substance; and,
   (c) evaporating the solvent.

9. The bioerodible controlled drug release device of claim 1 wherein said biologically active substance is a peptide.

10. The bioerodible controlled drug release device of claim 1 wherein said biologically active substance is a protein.

11. The bioerodible controlled drug release device of claim 1 wherein said biologically active substance is a steroid.

12. The bioerodible controlled drug release device of claim 1 wherein said biologically active substance is an antibiotic.

13. The bioerodible controlled drug release device of claim 1 wherein said device is adapted for subcutaneous implantation in an animal.

14. The bioerodible controlled drug release device of claim 1 wherein said device is adapted for transdermal administration of said biologically active substance.

15. A bioerodible controlled release device adapted for dispensing at least one biologically active substance at a controlled rate comprising a homogeneous polymeric matrix of:
   (a) an effective amount of at least one biologically active substance; and
   (b) a hydrophobic polyanhydride copolymer having a weight average molecular weight greater than 20,000 and an intrinsic viscosity greater than 0.3 dl/g in chloroform at 23° C., said polyanhydride produced from at least one dicarboxylic acid selected from the group consisting of:
   aliphatic dicarboxylic acids having the formula:

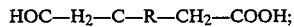

aromatic dicarboxylic acids having the formula:

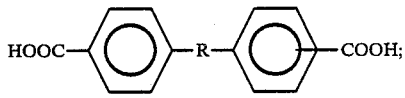

aromatic dicarboxylic acids having the formula:

aliphatic-aromatic dicarboxylic acids having the formula:

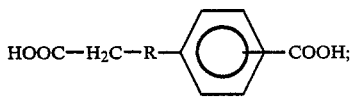

aromatic and aliphatic heterocyclic dicarboxylic acids having the formula:

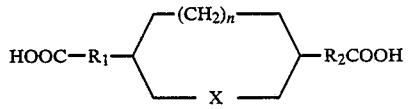

nitrogen and sulfur, and
   wherein
   X is selected from the group consisting of oxygen,
   n is an integer between 1 and 3; and
   aromatic and aliphatic heterocyclic dicarboxylic acids of the above formula in combination with at least one dicarboxylic acid selected from the group consisting of aliphatic dicarboxylic acids, aromatic-aliphatic dicarboxylic acids, and aromatic dicarboxylic acids having more than one phenyl group;
   wherein the R groups are divalent organic radical groups, wherein said polyanhydride includes at least 5% aromatic repeating units.

16. The bioerodible controlled release device of claim 15 wherein said polyanhydride copolymer includes at least 20% aromatic repeating units.

17. A bioerodible composition comprising at least one biologically active substance and a high molecular weight polyanhydride having a molecular weight greater than 20,000, an intrinsic viscosity greater than 0.3 dl/g in chloroform at 23° C., said polyanhydride having at least 20% aromatic repeating units.

18. The bioerodible composition of claim 17 wherein said bioerodible composition and biologically active substance is a homogeneous polymeric matrix.

* * * * *

UNITED STATES PATENT AND TRADEMARK OFFICE
CERTIFICATE OF CORRECTION

PATENT NO. : 4,888,176
DATED : December 19, 1989
INVENTOR(S) : Robert S. Langer, et al It is certified that error appears in the above-indentified patent and that said Letters Patent is hereby corrected as shown below:

On the title page, item [75] Inventors:

Delete "Robert S. Langer, Sommerville; Abraham J. Domb, Brookline; Cato T. Laurencin, Cambridge, all of Mass." and insert in place thereof --Robert S. Langer, Sommerville, Mass.; Edith Mathiowitz, Brookline, Mass.; Abraham J. Domb, Baltimore, Maryland; Cato T. Laurencin, Sommerville, Mass.--.

Column 1, line 10, change "May 24, 1984" to --May 21, 1984--.
Column 11, line 22, replace "Cd(CH3COO)$_2$" with --Cd(CH$_3$COO)$_2$--.
Column 16, line 42, replace "fil" with --film--.
Column 18, line 56, replace "an inorganic solvent at room temperature" with --chloroform at 23°C--.
Column 18, line 51, after "anhydride" add --; and--.
Column 19, line 58, replace "HOC-H$_2$-C-R-CH$_2$-COOH" with --HOOC-H$_2$C-R-CH$_2$-COOH--.
Column 20, line 32, delete "nitrogen and sulfur, and".
Column 20, line 34, after "oxygen," insert --nitrogen and sulfur, and--.

Signed and Sealed this

Seventh Day of June, 1994

Attest:

BRUCE LEHMAN

Attesting Officer          Commissioner of Patents and Trademarks